United States Patent
Koh et al.

(10) Patent No.: US 7,778,708 B1
(45) Date of Patent: Aug. 17, 2010

(54) DIAGNOSING CARDIAC HEALTH USING HISTOGRAM ANALYSIS OF THORACIC IMPEDANCE

(75) Inventors: Steve Koh, South Pasadena, CA (US); Rose Province, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 426 days.

(21) Appl. No.: 11/107,221

(22) Filed: Apr. 14, 2005

(51) Int. Cl.
*A61N 1/00* (2006.01)
*A61B 5/04* (2006.01)

(52) U.S. Cl. ........................................ 607/17; 600/513
(58) Field of Classification Search ............... 607/17, 607/37
See application file for complete search history.

(56) References Cited

U.S. PATENT DOCUMENTS

| | | | |
|---|---|---|---|
| 5,300,093 A | 4/1994 | Koestner et al. | 607/32 |
| 5,755,742 A * | 5/1998 | Schuelke et al. | 607/27 |
| 5,957,861 A | 9/1999 | Combs et al. | 600/547 |
| 6,104,949 A * | 8/2000 | Pitts Crick et al. | 600/547 |
| 6,512,949 B1 | 1/2003 | Combs et al. | 600/547 |
| 6,572,557 B2 | 6/2003 | Tchou et al. | 600/483 |
| 6,595,927 B2 | 7/2003 | Pitts-Crick et al. | 600/529 |
| 6,741,885 B1 | 5/2004 | Park et al. | 600/509 |
| 6,752,765 B1 * | 6/2004 | Jensen et al. | 600/536 |
| 7,065,403 B1 * | 6/2006 | Mouchawar et al. | 607/8 |
| 2003/0023184 A1 | 1/2003 | Pitts-Crick et al. | 600/547 |
| 2004/0102712 A1 | 5/2004 | Belalcazar et al. | 600/547 |

FOREIGN PATENT DOCUMENTS

| | | |
|---|---|---|
| EP | 1011802 B1 | 1/1998 |
| WO | WO 98/33553 | 1/1998 |
| WO | WO 01/19426 A2 | 3/2001 |
| WO | WO 2004/047638 A1 | 6/2004 |

* cited by examiner

*Primary Examiner*—Mark W Bockelman
*Assistant Examiner*—Elizabeth K So

(57) ABSTRACT

Diagnosing a patient's cardiac health through histogram analysis of thoracic impedance is described. Data values indicative of thoracic impedance are measured from a patient over a sample period that includes multiple respiratory cycles. The values are distributed across multiple bins of a histogram. A diagnostic value for use in diagnosing a patient's cardiac health is derived from values in one or more of the bins. As one example, a diagnostic value representing minimum thoracic impedance during the sample period can be derived from values in the lowest-valued bins. Diagnostic values can be computed for multiple sample periods in the same fashion. A trend analysis is performed on the diagnostic values to determine whether the patient's cardiac condition is improving or worsening. The trend may be presented in a graphical form to provide a visual tool for assessing the patient's condition over time.

9 Claims, 6 Drawing Sheets

DIAGNOSING CARDIAC HEALTH USING HISTOGRAM ANALYSIS OF THORACIC IMPEDANCE

TECHNICAL FIELD

The present invention generally relates to implantable devices and diagnostic systems for diagnosing a patient's cardiac health.

BACKGROUND

Heart failure is a condition in which the heart is unable to pump enough blood to sustain normal bodily functions. Heart failure may affect either the right side, left side, or both sides of the heart. As pumping action is lost, blood may back up into other areas of the body, including the liver, gastrointestinal tract, and extremities (right-sided heart failure), or the lungs (left-sided heart failure). Structural or functional causes of heart failure include high blood pressure (hypertension), valvular heart disease, congenital heart diseases, cardiomyopathy, heart tumor, and other heart diseases. Precipitating factors include infections with high fever or complicated infections, use of negative inotropic drugs (such as beta-blockers and calcium channel blocker), anemia, irregular heartbeats (arrhythmias), hyperthyroidism, and kidney disease.

Implantable cardiac devices, such as pacemakers and defibrillators, monitor many different cardiac parameters that may be used to determine how well a patient's heart is functioning. For instance, implantable cardiac devices can measure morphology-related parameters, impedance, intrinsic heart rate, heart rate recovery, heart rate variability, conduction delay, pressure, posture, activity, and so forth. Each of these parameters can be used to evaluate the patient's heart.

The implantable cardiac devices are commonly configured to stimulate the heart with pulses in response to individual or combinations of these measured parameters. Additionally, the devices can store these measured parameters over time and periodically transmit the measured parameters to external diagnostic systems for more exhaustive analysis. Unfortunately, in some instances, it can be difficult to derive meaningful values from the measured parameters.

In one such example, the measured values of some parameters are difficult to interpret due to variations caused by other factors, such as bodily functions or patient activity. For example, measured thoracic impedance values decrease when a ratio of fluid to air in a sensed region of the thorax increases. Such a condition occurs when the patient experiences pulmonary edema. However, such a condition also occurs when the patient exhales. It is difficult to interpret measured thoracic impedance values due to the multiple possible factors affecting the measured parameter. Accordingly, there is a need to process individual parameters in a way that assists in diagnosing the patient's cardiac health.

SUMMARY

Diagnosing a patient's cardiac health through histogram analysis of thoracic impedance is described. Data values indicative of thoracic impedance are measured from a patient over a sample period that includes multiple respiratory cycles. The values are distributed across multiple bins of a histogram. A diagnostic value for use in diagnosing a patient's cardiac health is derived by processing values in one or more of the bins. As one example, a diagnostic value representing minimum thoracic impedance during the sample period can be derived by processing values in the lowest-valued bins.

Diagnostic values can be computed for multiple sample periods in the same fashion. A trend analysis is performed on the diagnostic values to determine whether the patient's cardiac condition is improving or worsening. The trend may be presented in a graphical form to provide a visual tool for assessing the patient's condition over time. A care provider can then make a more informed decision as to how to treat the patient, including weighing such factors as whether to prescribe a new therapy or alter an existing one.

DETAILED DESCRIPTION

Overview

Figure 1:
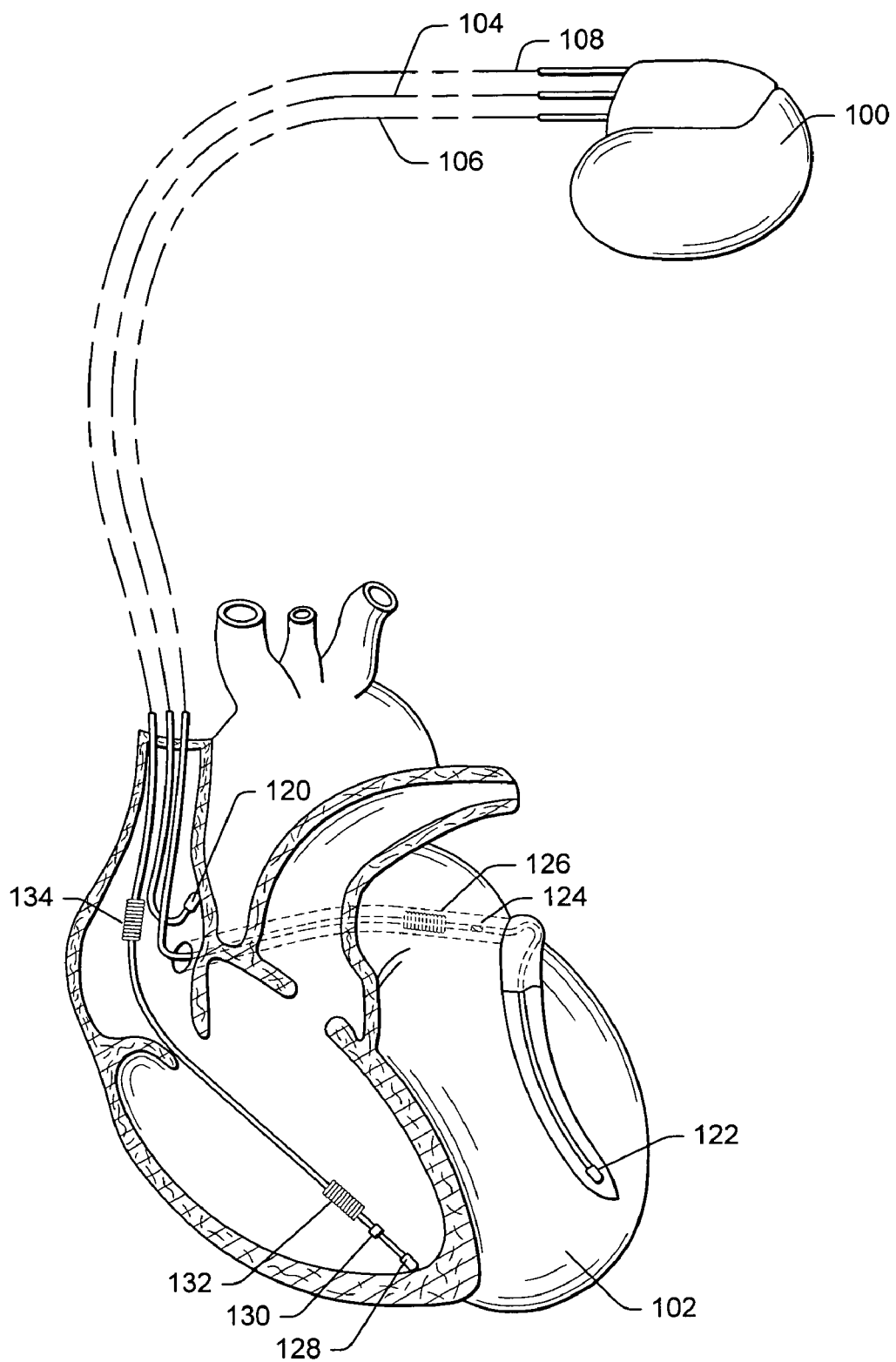
FIG. 1 is a diagrammatic illustration of an implantable cardiac device in electrical communication with a patient's heart for multi-chamber sensing and delivery of multi-chamber stimulation and shock therapy.

The following discussion describes techniques for diagnosing a patient's cardiac health. A set of measured parameter values from a sample period is analyzed using a histogram to determine a diagnostic value for use in the diagnosis. The diagnostic value is more prognostic of the patient's condition during the sample period than the measured values. The diagnostic value is especially valuable where multiple factors may influence the measured parameter values and it would otherwise be difficult to isolate the affects of the individual factors on the parameter values. In such an instance, the ability to remove one or more such factors proves useful in evaluating the patient's cardiac condition.

One particular case in point is thoracic impedance, which is commonly measured as an indicator of a patient's cardiac health. Direct measurements of thoracic impedance are affected by many factors, including the patient's natural respiration. Measurement values that might suggest that a patient is experiencing pulmonary edema also occur when the patient exhales. For various reasons which will not be elaborated here, it is difficult to determine the degree to which the patient's respirations are affecting individual measured thoracic impedance values.

The histogram analysis described in this document processes thoracic impedance measurements to determine a diagnostic value that is less impacted by such influencing factors. Data values indicative of thoracic impedance are measured from a patient over a sample period that includes multiple respiratory cycles. The values are distributed across multiple bins of a histogram. The diagnostic value is derived from values in one or more of the bins. For instance, a diagnostic value representing minimum thoracic impedance during the sample period can be derived from values in the lowest-valued bins of the histogram. The minimum thoracic impedance value determined by this technique is more valuable in assessing the patient's condition since the degree of influence of the patient's respirations is reduced or obviated altogether.

The histogram analysis technique can be repeated for multiple sample periods to determine minimum impedance values for each of the individual sample periods. The technique can then derive a trend of the minimum values, which can be used to indicate whether a pulmonary edema condition of the patient is improving or worsening. Such a trend, either taken alone or in combination with other parameter trends, can be indicative of the patient's cardiac condition.

For discussion purposes, the histogram analysis techniques are described in the context of diagnosing cardiac health, such as pulmonary edema. The parameters are measured using an implantable cardiac device. Processing of the parameters can be implemented within the implantable device (assuming it is configured with sufficient memory and processing capabilities) or alternatively at an external device, such as a programmer or diagnostic computing system.

Implantable cardiac devices are commonly characterized as a miniature computing device that is implanted into the body of a patient to monitor, regulate, and/or correct heart activity. Such devices include implantable cardiac stimulation devices (e.g., implantable cardiac pacemakers, implantable defibrillators, cardiac rhythm management devices) that apply stimulation therapy to the heart and implantable cardiac monitors that monitor and record heart activity for diagnostic purposes. The following discussion describes an exemplary implantable cardiac device and diagnostic system that implements a histogram analysis sub-system.

Implantable Cardiac System

FIG. 1 shows an exemplary implantable cardiac device 100 in electrical communication with a patient's heart 102 for monitoring heart activity and/or delivering stimulation therapy, such as pacing therapies. Three leads—a right atrial lead 104, a coronary sinus lead 106, and a right ventricular lead 108—interconnect the device 100 with the patient's heart 102 to support multi-chamber detection and stimulation therapy.

The right atrial lead 104 supports an atrial tip electrode 120, which typically is implanted in the patient's right atrial appendage. The right atrial lead 104 enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 is used for shocking therapy.

The right ventricular lead 108 is electrically coupled to a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

Figure 2:
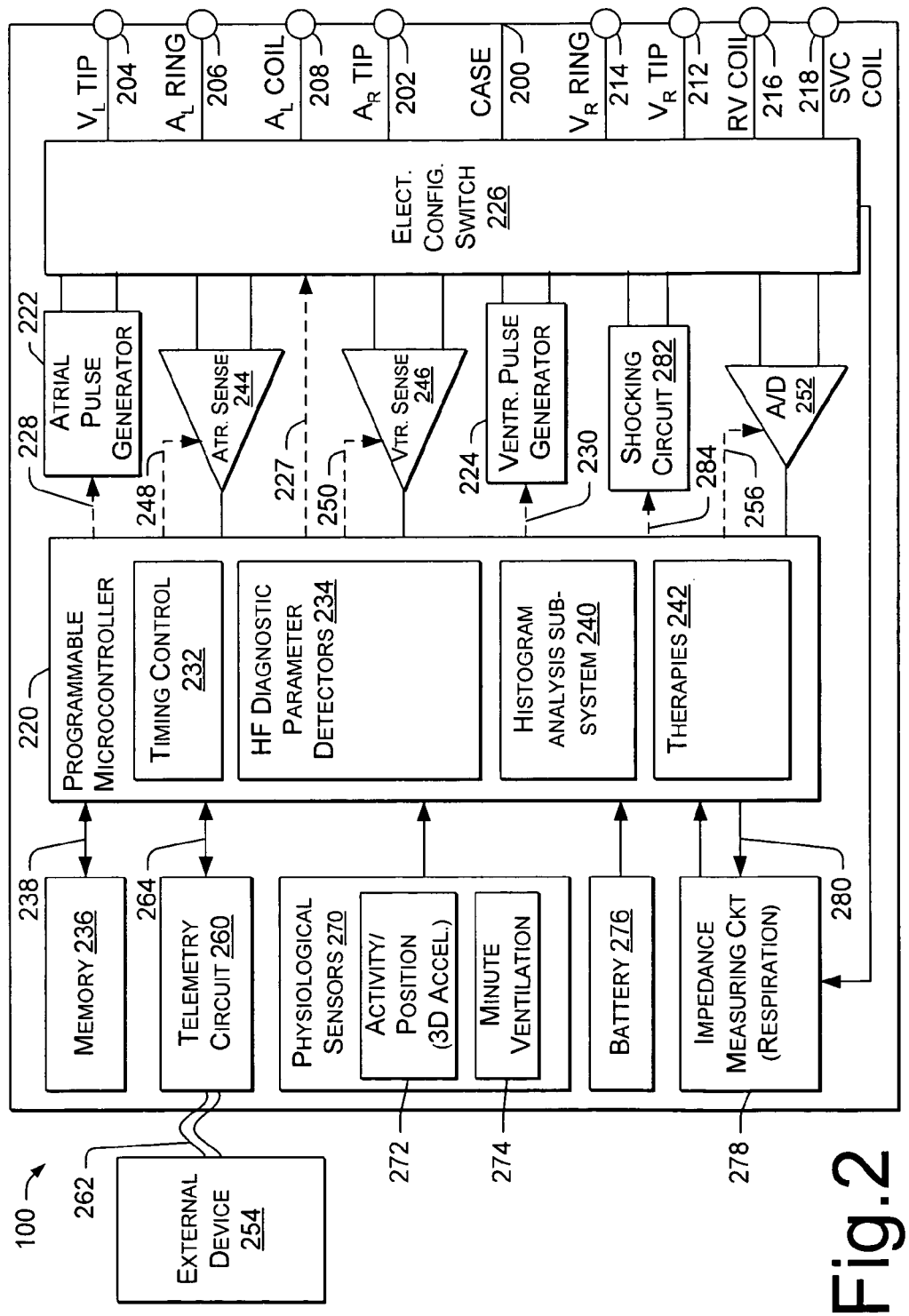
FIG. 2 is a functional block diagram of the multi-chamber implantable cardiac device.

FIG. 2 shows an exemplary, simplified block diagram depicting various components of the implantable cardiac device 100. The components are housed in housing 200, which is often referred to as the "can", "case", "encasing", or "case electrode". Housing 200 may be programmably selected as a return electrode for unipolar modes or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals), including:

a right atrial tip terminal (AR TIP) 202 for atrial tip electrode 120;
a left ventricular tip terminal (VL TIP) 204 for left ventricular tip electrode 122;
a left atrial ring terminal (AL RING) 206 for left atrial ring electrode 124;
a left atrial shocking terminal (AL COIL) 208 for left atrial coil electrode 126;
a right ventricular tip terminal (VR TIP) 212 for right ventricular tip electrode 128;
a right ventricular ring terminal (VR RING) 214 for right ventricular ring electrode 130;
a right ventricular shocking terminal (RV COIL) 216 for RV coil electrode 132; and
an SVC shocking terminal (SVC COIL) 218 for SVC coil electrode 134.

The implantable cardiac device 100 includes a programmable microcontroller 220 that controls various operations, including cardiac monitoring and stimulation therapy. Microcontroller 220 includes a microprocessor (or equivalent control circuitry), RAM and/or ROM memory, logic and timing circuitry, state machine circuitry, and I/O circuitry.

Device 100 further includes an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. The switch 226 includes multiple switches for connecting the desired electrodes to the appropriate I/O circuits, thereby providing complete electrode programmability. Accordingly, switch 226, in response to a control signal 227 from the microcontroller 220, determines the polarity of the stimulation pulses (e.g., unipolar, bipolar, combipolar, etc.) by selectively closing the appropriate combination of switches. To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 is illustrated as including timing control circuitry 232 to control the timing of the stimulation pulses (e.g., pacing rate, atrio-ventricular (AV) delay, atrial interconduction (A-A) delay, or ventricular interconduction (V-V) delay, etc.). The timing control circuitry may also be used for the timing of refractory periods, blanking intervals, noise detection windows, evoked response windows, alert intervals, marker channel timing, and so on.

Microcontroller 220 is also equipped with multiple detectors 234 used to detect or compute parameters indicative or predictive of heart failure (HF). Examples of HF parameter detectors 234 include an arrhythmia detector to detect arrhythmia parameters, a morphology detector to detect morphological parameters, impedance circuitry to detect DC impedance (e.g., transthoracic impedance), activity sensor to detect activity variance, posture sensors to sense posture or patient position, exercise compliance monitor to evaluate exercise compliance, heart rate detectors to detect heart rate and heart rate variability, pressure sensors to detect pressure, and so forth. It is noted that these detectors are examples, and others may be employed. Essentially, the microcontroller 220 may implement any detector that produces a parameter that may be used alone or in combination with another to predict or diagnose heart failure.

The HF parameters are stored in memory 236, which is coupled to the microcontroller 220 via a suitable data/address bus 238. In addition to these parameters, the memory 236 stores programmable operating parameters used by the microcontroller 220 to customize the operation of the device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

Microcontroller 220 also implements a histogram analysis sub-system 240 that evaluates one or more of the multiple HF diagnostic parameters collected by the HF parameter detectors 234. The histogram analysis sub-system analyzes parameters measured over a sample period that includes multiple respiration cycles. The parameter values are distributed across multiple bins of a histogram. The sub-system 240 derives a diagnostic value from the parameter values in one or more of the bins. As one example, a diagnostic value representing minimum thoracic impedance during the sample period can be derived by processing values in the lowest-valued bins. The sub-system 240 can further derive a trend of the diagnostic values computed from multiple sample periods. The trends of individual parameters may be suggestive of the patient's cardiac health.

The results produced by the histogram analysis can provide more meaningful information and/or more easily discernable information to the clinicians than was previously available. For example, the analysis can convey a trend relating to pulmonary edema. In such an example, by determining a minimum thoracic impedance value for multiple data sets relating to transthoracic impedance, the histogram analysis sub-system can assess from the trend whether the patient's pulmonary edema is improving or worsening. Thus, such a trend alone or combined with other parameters can be indicative of the patient's cardiac condition.

The microcontroller 220 may further be programmed to prescribe one or more pacing therapies 242 in response to results from the histogram analysis sub-system 240. For example, if the histogram analysis sub-system 240 predicts that conditions are worsening and heart failure may be imminent, the microcontroller 220 may prescribe a pacing therapy that attempts to counteract the parameters suggesting a worsening condition.

The components 234, 240, and 242 may be implemented in hardware as part of the microcontroller 220, or as software/firmware instructions programmed into the device and executed on the microcontroller 220 during certain modes of operation. These components may further be implemented independent from the microcontroller 220. Although not shown, the microcontroller 220 may further include other dedicated circuitry and/or firmware/software components that assist in monitoring various conditions of the patient's heart and managing pacing therapies.

The implantable cardiac device 100 has atrial sensing circuits 244 and ventricular sensing circuits 246 to detect the presence of cardiac activity in each of the four chambers of the heart. The sensing circuits 244 and 246 may be selectively coupled to the right atrial lead 104, coronary sinus lead 106, and the right ventricular lead 108 through the switch 226. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity. Each sensing circuit 244 and 246 may employ one or more low power, precision amplifiers with programmable gain and/or automatic gain control, band pass filtering, and threshold detection circuitry to selectively sense the cardiac signal of interest. The automatic gain control enables the device 100 to sense low amplitude signal characteristics of atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224 in response to the absence or presence of cardiac activity in the appropriate chambers of the heart. The sensing circuits 244 and 246 receive control signals from the microcontroller 220 over signal lines 248 and 250 for purposes of controlling the gain, threshold, polarization charge removal circuitry (not shown), and the timing of any blocking circuitry (not shown) coupled to the inputs of the sensing circuits.

The implantable cardiac device 100 is further equipped with an analog-to-digital (ND) data acquisition system 252 to sample cardiac signals across any pair of desired electrodes. The system 252 is coupled to the right atrial lead 104, the coronary sinus lead 106, and the right ventricular lead 108 through the switch 226. Cardiac signals received from the leads are supplied to the data acquisition system 252, which is configured to acquire intracardiac electrogram (IEGM) signals, convert the raw analog data into a digital signal, and store the digital signals for processing.

The data acquisition system 252 is coupled to the microcontroller 220, or other detection circuitry, to assist in detecting various parameters and events. For instance, the system 252 acquires the signals used by the HF parameter detectors 234 to detect parameters indicative or suggestive of heart failure. The data acquisition system 252 is further configured to detect an evoked response from the heart 102 in response to an applied stimulus, which is otherwise known as detecting "capture". Capture occurs when an electrical stimulus applied to the heart is of sufficient energy to depolarize the cardiac tissue, thereby causing the heart muscle to contract. The microcontroller 220 detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determines if capture has occurred.

Capture detection may occur on a beat-by-beat basis or on a sampled basis. A capture threshold search can desirably be performed, once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The data acquired by the data acquisition system 252 is stored in memory 236 and can be subsequently transmitted to an external device 254. The external device 254 may be implemented in many ways, including as a programmer, a transtelephonic transceiver, or a diagnostic system analyzer. Additionally, the external device 254 may be representative of an intermediate communication device that receives information from the implantable device and relays the information to another device or system for evaluation. In this manner, the HF diagnostic parameters and/or the results of any histogram analysis sub-system may be output to the external device 254 for further analysis or presentation to the clinician.

In one implementation, a telemetry circuit 260 facilitates communication between the implantable device 100 and the external device 254. During programming or data output, the telemetry circuit 260 establishes a communication link 262 with the external device 254. In addition to downloading data to the external device, operating parameters for the implantable device 100 may be non-invasively programmed into the memory 236 by transmission from the external device 254 over link 262 and through the telemetry circuit 260. The microcontroller 220 activates the telemetry circuit 260 with a control signal 264. The telemetry circuit 260 allows intracardiac electrograms and status information relating to the operation of the device 100 (as contained in the microcontroller 220 or memory 236) to be sent to the external device 254 through an established communication link 262.

The implantable device 100 may include magnet detection circuitry (not shown), coupled to the microcontroller 220, to detect when a magnet is placed over the device 100. A magnet may be used by a clinician to perform various test functions of the device 100 and/or to signal the microcontroller 220 that the external programmer 254 is in place to receive or transmit data to the microcontroller 220 through the telemetry circuit 260.

The implantable cardiac device 100 can further include one or more physiologic sensors 270. Such sensors are commonly referred to as "rate-responsive" sensors because they are typically used to adjust pacing stimulation rates according to the exercise state of the patient. However, the physiological sensor(s) 270 may further be used to detect changes in cardiac output, changes in the physiological condition of the heart, diurnal changes in activity (e.g., detecting sleep and wake states), or respiration activity (e.g., minute ventilation). The microcontroller 220 responds to changes sensed by the sensor (s) 270 by adjusting various pacing parameters (such as rate, AV Delay, V-V Delay, etc.) at which the atrial and ventricular pulse generators 222 and 224 generate stimulation pulses. While shown as being included within the device 100, the physiologic sensor(s) 270 may also be external to the device 100, yet still be implanted within or carried by the patient. Examples of physiologic sensors that may be implemented in device 100 include sensors that, for example, sense respiration activities, $O_2$ saturation, evoked response, pH of blood, and so forth.

In the illustrated implementation, the physiological sensors 270 include sensors for detecting patient activity and respiration. Any sensor capable of sensing such conditions, either directly or indirectly, may be used. In particular, the physiological sensors 270 include an activity sensor 272 to detect patient movement. The activity sensor 272 may be implemented in many ways, including as a three-dimensional (3D) DC accelerometer. In one configuration, the accelerometer output signal is bandpass-filtered, rectified, and integrated at regular timed intervals. The processed accelerometer signal is used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting state. The activity variance can be monitored diurnally to detect the low variance in the measurement corresponding to the sleep state.

An exemplary physiological sensor used to detect respiratory conditions is a minute ventilation (MV) sensor 274. The MV sensor 274 senses minute ventilation, which is the total volume of air that moves into and out of a patient's lungs in a minute. The MV sensor 274 uses transthoracic impedance, which is a measure of impedance across the chest cavity, to sense air movement. Lungs filled with air have higher impedance than empty lungs. Thus, upon inhalation, impedance increases and upon exhalation, impedance decreases. Other respiration sensors that may be used in addition to, or instead of, the MV sensor 274 include an $O_2$ sensor that measures oxygen-related parameters, a sensor to measure respiration rate, and a sensor to measure tidal volume.

The activity and respiratory signals generated by the sensors 270 are passed to the microcontroller 220 for measurement by the HF parameter detectors 234. Such signals can be used to determine HF diagnostic parameters that may be used in evaluation of the patient's heart and possible heart failure. The histogram analysis sub-system 240 analyzes trends in the HF diagnostic parameters from the detectors 234 to produce results that may be used by a clinician as a proxy for whether the heart condition is worsening or improving. If a worsening condition is determined, the microcontroller 220 may prescribe a pacing therapy 242 and/or may generate an alert that the patient requires attention.

The implantable cardiac device 100 additionally includes a battery 276 to supply operating power to various components shown in FIG. 2. The battery 276 is capable of operating at low current drains for long periods of time (e.g., less than 10 μA), and is capable of providing high-current pulses (for capacitor charging) when the patient requires a shock pulse (e.g., in excess of 2 A, at voltages above 2 V, for periods of 10 seconds or more). The battery 276 also has a predictable discharge characteristic so that elective replacement time can be detected. As one example, the device 100 employs lithium/ silver vanadium oxide batteries.

The implantable cardiac device 100 further includes an impedance measuring circuit 278 that is enabled by the microcontroller 220 via a control signal 280. The impedance measuring circuit 278 is used to measure impedance data, including transthoracic impedance. As one example implementation, the impedance measure circuit 278 may be implemented to perform a high voltage lead integrity check (HVLIC) to check the integrity of a lead by measuring impedance. The HVLIC can then be used as a surrogate measurement for fluid in the lung. The impedance measuring circuit 278 may also be configured to measure impedance using a constant injection technique. With this technique, a constant current is applied to leads and a voltage is measured as a surrogate of thoracic impedance, which changes over the respiration cycle, The impedance measure circuit 278 may also be used for other purposes, including: lead impedance surveillance during the acute and chronic phases for proper lead positioning or dislodgement; detecting operable electrodes and automatically switching to an operable pair if dislodgement occurs; measuring thoracic impedance for many uses including determining shock thresholds; detecting when the device has been implanted; measuring stroke volume; and detecting the opening of heart valves; and so forth. The impedance measuring circuit 278 can be used to measure respiration-related parameters, such as respiration rate, minute ventilation, respiration signal amplitude, and tidal volume. The impedance measuring circuit 278 is coupled to the switch 226 so that any desired electrodes may be used.

The device 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 Joules), moderate (e.g., 0.5-10 Joules), or high energy (e.g., 11 to 40 Joules), as controlled by the microcontroller 220. Such shocking pulses are applied to the patient's heart 102 through at least two shocking electrodes selected, for example, from the left atrial coil electrode 126, the RV coil electrode 132, and/or the SVC coil electrode 134. As noted above, the housing 200 may act as an active electrode in combination with the RV coil electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Diagnostic System

In the above described implementation, the histogram analysis sub-system is implemented within the implantable cardiac device 100. In other implementations, the histogram analysis sub-system may be partially or fully implemented in computing devices external to the implantable device 100. For instance, the histogram analysis sub-system may be implemented in an external programmer or in diagnostic computers used by the clinician to analyze parameters suggestive of heart failure. One such system implementation is described below.

Figure 3:
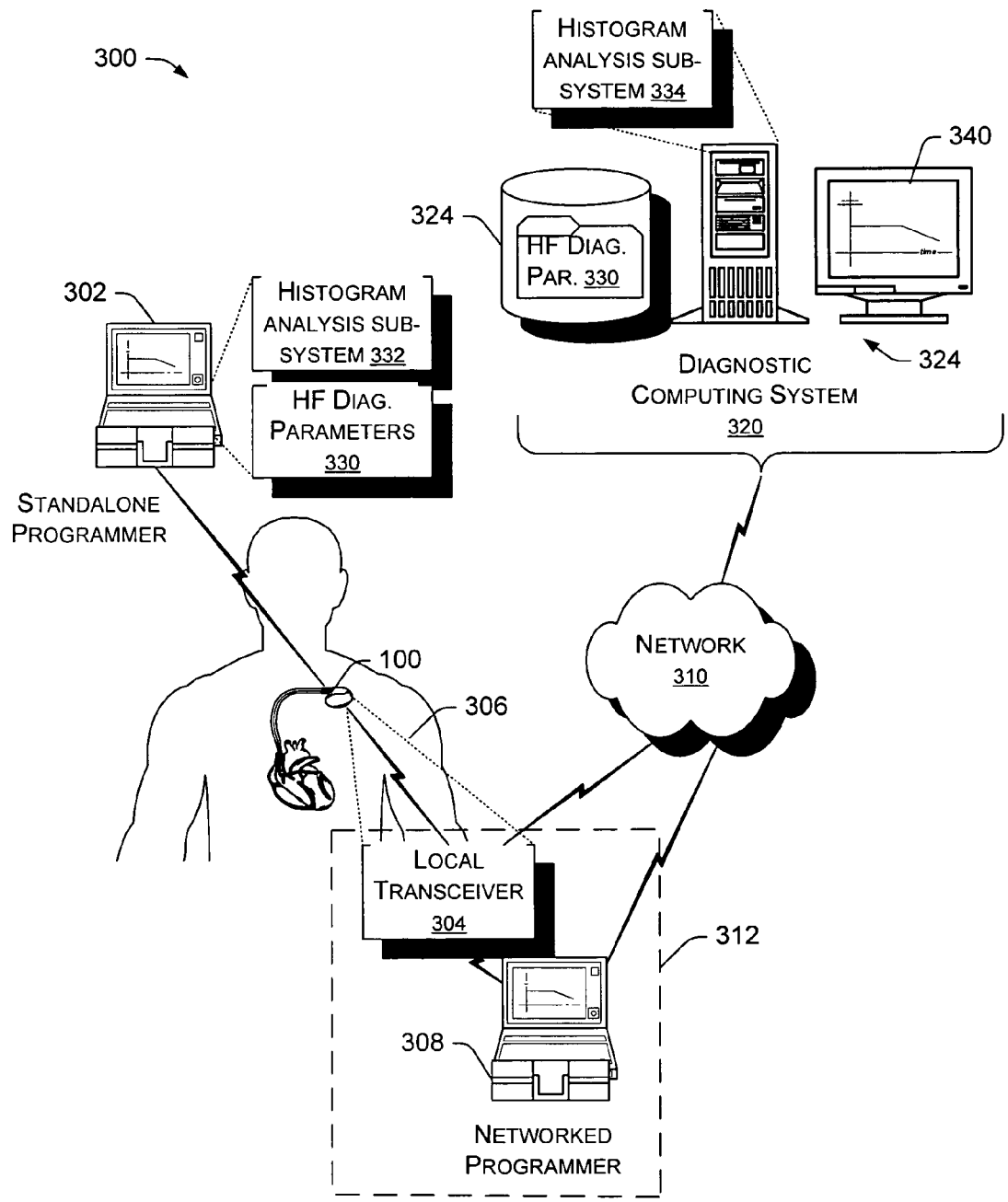
FIG. 3 is a diagrammatic illustration of a diagnostic system where the implantable cardiac device transmits data to one or more external devices for further processing.

FIG. 3 shows an HF diagnostic system 300 that includes the implantable cardiac device 100 in communication with one or more external devices that are capable of conducting diagnostics on data parameters received from the implantable device. The implantable device 100 measures and stores parameters over time. Depending upon the size of the memory, the device may store parameters collected over many days or months. The parameters are then occasionally transmitted from the device 100 to one or more external devices. The data may be downloaded, for example, during clinician checkups or other specified times. The external devices are configured with more processing and memory capabilities than the implantable device, and hence are able to conduct a more exhaustive analysis of the parameters.

The external devices may be implemented as a programmer, a computer, and/or a network of computing systems and data storages units. In this illustration, the implantable device 100 communicates with a standalone or offline programmer 302 via short-range telemetry technology. The offline programmer 302 is equipped with a wand that, when positioned proximal to the device 100, communicates with the device 100 through a magnetic coupling.

The implantable cardiac device 100 can alternatively, or additionally, be configured to communicate with a local transceiver 304 that is proximally located near the patient. The local transceiver 304 may be configured as an electronic communication device that is worn by the patient or is situated proximal to the patient, such as on a structure within the room or residence of the patient. The local transceiver 304 communicates with the implantable device 100 using short-range telemetry or longer-range high-frequency-based telemetry, such as RF (radio frequency) transmissions. Alternatively, the local transceiver 304 may be incorporated into the implantable device 100, as represented by dashed line 306. In this case, the device includes a separate and isolated package area that accommodates high-frequency transmissions without disrupting operation of the monitoring and stimulation circuitry.

The local transceiver 304 communicates with other external computing devices directly or via a network. In the illustrated implementation, the transceiver 304 transmits parameters received from the implantable device 100 to a networked programmer 308, which is connected to a network 310. The networked programmer 308 is similar in operation to standalone programmer 302, but differs in that it has a network port for connection to the network 310. The networked programmer 310 may be local to, or remote from, the local transceiver 304 depending upon the implementation and transmission range. Alternatively, the local transceiver 304 may be incorporated into the networked programmer 308, as represented by dashed line 312. Another possible implementation is for the local transceiver 304 to be connected directly to the network 310 for communication with remote computing devices and/or programmers including, for example, diagnostic computing system 320. Diagnostic computing system 320 includes one or more computers 334 for processing data received from the device 100 and a data store 324 for storing the device data.

The network 310 may be implemented by one or more different types of networks (e.g., Internet, local area network, wide area network, telephone, cable, satellite, etc.), including wire-based technologies (e.g., telephone line, cable, fiber optics, etc.) and/or wireless technologies (e.g., RF, cellular, microwave, IR, wireless personal area network, etc.). The network 310 can be configured to support any number of different protocols, including HTTP (HyperText Transport Protocol), TCP/IP (Transmission Control Protocol/Internet Protocol), WAP (Wireless Application Protocol), Bluetooth, and so on.

The HF diagnostic parameters detected by the device 100 and offloaded to the external devices for further analysis are stored at the external devices. In FIG. 3, the HF diagnostic parameters 330 are shown stored in programmer 302 and the data store 324 of computing system 320.

The external devices are equipped with a histogram analysis sub-system to process the parameters received from the device 100, as well as any other parameters that might warrant consideration when diagnosing a patient's health (e.g., a patient's weight, age, etc.). In this example, the standalone programmer 302 implements histogram analysis sub-system 332 to analyze the HF diagnostic parameters 330 that are stored locally, and the diagnostic computer 322 implements histogram analysis sub-system 334 to analyze the HF diagnostic parameters 330 stored in data store 324.

The histogram analysis sub-system determines a diagnostic value from a set of parameters received from device 100, such as parameters indicative of thoracic impedance. The parameters are measured by the implantable device 100 over a sample period that includes multiple respiratory cycles. The parameter values are distributed across multiple bins of a histogram and the diagnostic value is derived from values in one or more of the bins. As one example, a diagnostic value representing minimum thoracic impedance during the sample period can be derived from values in the lowest-valued bins. Diagnostic values may be computed for multiple sample periods, and a trend of those values may be developed. This trend provides an assessment as to whether the patient's cardiac health is improving or not.

In some instances, the histogram analysis sub-system can further trigger an appropriate responsive action, such as a change in pacing therapy or administration of defibrillation shocking pulses.

Alternatively or additionally, the sub-system can present diagnostic values and/or the trend to a care provider. The programmer 302 and/or computer 334 may present the results in a number of ways. One possibility is to present a user-perceptible image, such as a graphical user interface (UI), which depicts the trend to the clinician. One example screen 340 is shown depicted on diagnostic computer 334. In this example, the screen 340 depicts a graphical illustration of a trend indicating a worsening of a patient's pulmonary edema condition. A detailed example is described below in relation to FIG. 7. The graphical UI assists the care provider in more quickly ascertaining the patient's cardiac condition.

Histogram Analysis

The histogram analysis sub-system implemented by the implantable cardiac device 100 or an external device (e.g., programmer 302 and/or computer 334) receives multiple parameters detected by the implantable cardiac device 100. The sub-system uses histogram analysis to determine a diagnostic value for a sample period. Generally, the histogram analysis sub-system distributes the measured values from the sample period in appropriate bins of a histogram. The histogram analysis sub-system then selects a number of bins which correspond to a desired value. For instance, if a diagnostic value representing a maximum measured parameter is desired, one or more bins containing the highest measured values can be selected for further processing. The average of the measured values from the selected bins can be calculated to determine the diagnostic value. The diagnostic value is more prognostic of the patient's condition during the sample period than the measured values.

One exemplary process by which the histogram analysis sub-system can determine diagnostic values for sample periods is described in relation to FIGS. 4-7. In this example, the sub-system is attempting to identify a value indicative of minimum thoracic impedance. As mentioned above, thoracic impedance can be suggestive of varying degrees of fluid in the lungs, and hence useful in diagnosing pulmonary edema. More fluid in the lungs results in decreased impedance, while less fluid results in increased impedance. The patient's respirations complicate direct analysis of thoracic impedance, in that the values change depending on the respiration cycle. When the patient's lungs are filled with air, the impedance increases; and when the patient exhales the air, the impedance drops. Thus, it is difficult to know whether impedance is changing over time or merely reflective of respiration cycles. The technique described below uses histogram analysis to find minimum thoracic impedance values from the multiple sample periods over respiration cycles. These diagnostic values allow meaningful comparison of the patient's condition over time. Further processing of the values can provide a trend indicating whether fluid content in the patient's lungs is increasing or decreasing, which in turn provides insight as to whether the patient is experiencing pulmonary edema.

Figure 4:
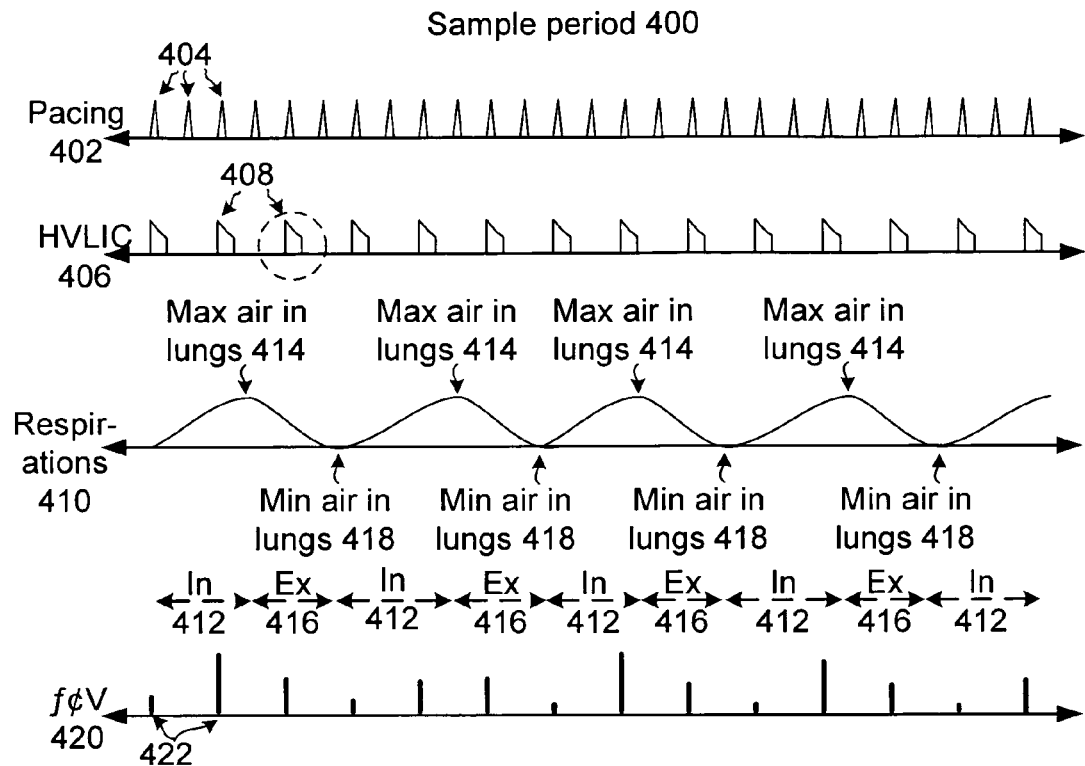
FIGS. 4-6 illustrate graphical representations of histogram analysis implemented in the diagnostic system of FIG. 3.

FIG. 4 shows several event timelines that occur within a sample period 400. Pacing timeline 402 shows pacing pulses 404 (not all of which are indicated with specificity) administered at intervals by an implantable cardiac device, such as device 100 in FIG. 1. Timeline 406 illustrates pulses 408 (not all of which are indicated with specificity) that are measured or sensed when performing a high voltage lead integrity check (HVLIC). A pulse is delivered to the patient and the sensed HVLIC pulse 408 captures the decay of the delivered pulse. In the illustrated timelines, an HVLIC pulse is administered with every other pacing pulse 404. However, other timing configurations can be used. For instance, an HVLIC pulse could be administered with every pacing pulse. In still another example, the HVLIC pulses could be delivered independent of the timing of the pacing pulses.

Figure 5:
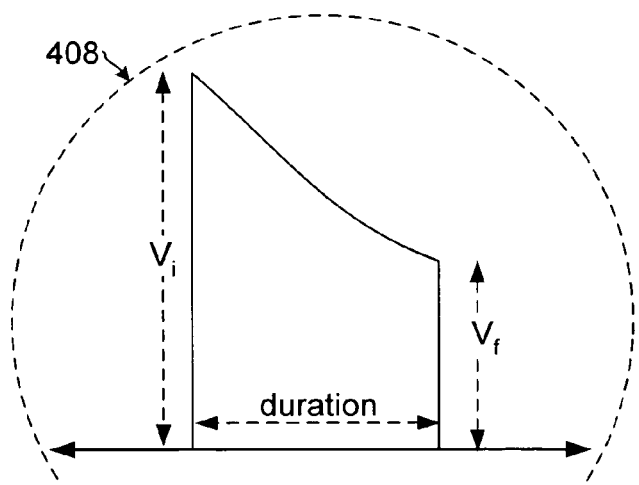

FIG. 5 illustrates a more detailed view of an individual sensed HVLIC pulse 408. An initial voltage ($V_i$) is applied and decays to final voltage ($V_f$) over a given duration. The difference in initial voltage and final voltage of the sensed HVLIC pulse 408 is one way to measure thoracic impedance at this particular temporal instant, as will be described below in more detail. Known techniques for calculating the voltage differential ($V_i-V_f$) can be utilized for the pulse as a whole and/or for individual subunits of the pulse.

It is noted that other data values indicative of thoracic impedance may be used in lieu of HVLIC. For instance, the implantable device can measure thoracic impedance using a constant injection technique in which a constant current is applied and a voltage is measured. With the current constant, the varying voltages are related to the changing impedance caused by the patient's inhalation and exhalation, and hence are reflective of thoracic impedance. Thus, the voltage parameters are an example of another set of data values that may be used in the histogram analysis described herein.

Returning to FIG. 4, respiration timeline 410 shows a series of respiration cycles of inhalation and exhalation. Inhalation 412 culminates in a maximum amount of air in the lungs indicated generally at 414. Exhalation 416 culminates in a minimum amount of air in the lungs as indicated generally at 418. In this instance, the pacing pulses 404 are generally synchronized with the patient's respirations so that about six pacing pulses are administered per respiration cycle. Other implementations may randomize the HVLIC pulses to ensure measured impedance values relative to a broad range of points in the respiration cycle.

Voltage drop ($\Delta V$) timeline 420 illustrates the calculated voltage drop 422 ($\Delta V=V_i-V_f$) for individual HVLIC pulses 408, such as that shown in FIG. 5. The voltage drop is indicative of the patient's thoracic impedance at a particular sample time. Larger spikes on the voltage drop time line 420 represent instances where $\Delta V$ is comparatively large, which correlates with times when the lungs are filled with air and impedance increases. Smaller spikes on the voltage drop time line 420 represent instances where $\Delta V$ is comparatively small, which correlates with times when the lungs empty and impedance decreases. These calculated voltage drop values are used by the histogram analysis sub-system as discussed in relation to FIG. 6.

Figure 6:
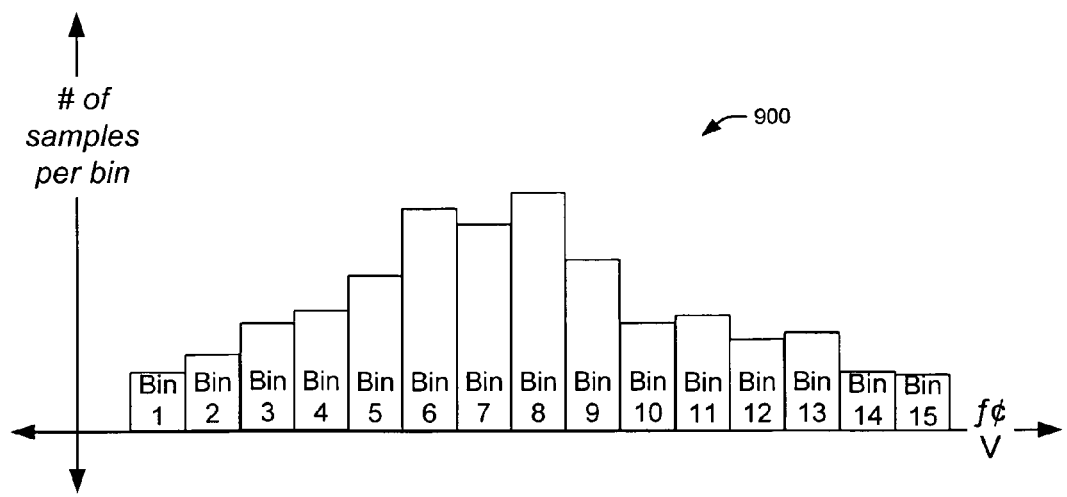

FIG. 6 illustrates a histogram 900 formed by the histogram analysis sub-system to determine a diagnostic value for a particular sample period of measured or sensed parameter values. In this example, histogram 900 is composed of 15 bins. The number of bins can be adjusted in a particular application as long as the same number and value of bins is used for each set of sample periods being compared. In some instances, the histogram analysis sub-system determines the number of bins. Alternatively or additionally, a user-interface may allow a clinician to adjust the number of bins.

Assume for purposes of explanation that bin 1 is assigned for voltage drop values 422 (FIG. 4) of 1.0-1.1, bin 2 is assigned for values of 1.1-1.2, and so on with bin 15 holding assigned values of 2.4-2.5. In this manner, the smallest voltage drops representing the lowest impedance measurements are placed in the lowered number bins 1, 2, and 3, and the largest voltage drops representing the highest impedance measurements are placed in the higher number bins 13, 14, and 15.

Now, suppose that the diagnostic value of interest is minimum thoracic impedance, which is represented by one or more of the lower numbered bins. The histogram analysis sub-system determines the minimum thoracic impedance by computing a representative value from the $\Delta V$ values placed in one or more selected low-numbered bins. For instance, suppose the histogram analysis sub-system selects bins 1 and 2. The number of bins and the assigned bin values can be adjusted as long as they remain consistent when computing diagnostic values to be compared over several sample periods. In this example, assume for purposes of explanation that bin 1 contains four $\Delta V$ values of 1.02, 1.03, 1.04 and 1.07 and that bin 2 contains eight $\Delta V$ values of 1.11, 1.13, 1.15, 1.15, 1.16, 1.16, 1.17, and 1.19. The summation of the selected bins equals the sum of the values of bin 1 plus the sum of the values of bin 2. This total value is then divided by the total number of values in the selected bins.

$\Sigma(\Delta V)$ for selected bins (bin 1 and bin 2)=((Total value of ($\Delta V$) in bin 1)+(Total value of ($\Delta V$) in bin 2))/total number of $\Delta V$ values in selected bins ((1.02+1.03+1.04+1.07)+(1.11+1.13+1.15+1.15+1.16+1.16+1.17+1.19))/12

((4.16)+(9.22))/12=1.115

In this example, the diagnostic value for this sample period is 1.115, which is representative of the minimum impedance value for this sample period. With this approach, the histogram analysis sub-system has effectively removed variability caused by the patient's breathing to ascertain a minimum impedance value over several respiratory cycles. The histogram analysis sub-system can similarly determine a diagnostic value for other sample periods, thereby tracking the value over a period of time (e.g., days, weeks, or months). The histogram analysis sub-system can then use the diagnostic values determined from the various sample periods to derive a trend relating to the cardiac health of the patient, such as pulmonary edema.

Figure 7:
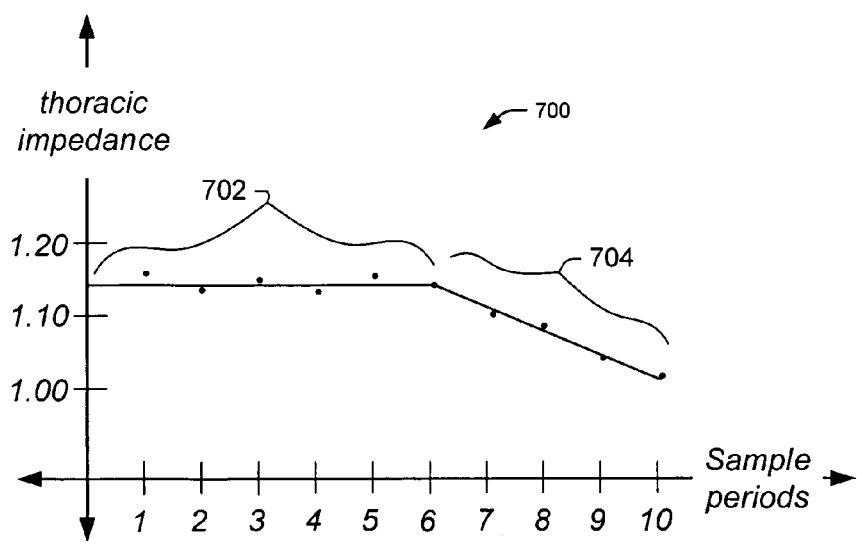
FIG. 7 illustrates graphical representations of a trend derived by the diagnostic system when histogram analysis is performed on thoracic impedance values.

FIG. 7 illustrates a graphical representation 700 of diagnostic thoracic impedance values determined for 10 different sample periods. As one example, one sample period might be obtained each day for 10 days, with the first sample period having a diagnostic value of 1.115 as determined above in relation to FIGS. 4-6. The histogram analysis sub-system derives a trend from the 10 diagnostic values. As indicated generally at 702, the trend indicates a generally static condition in days one through six. This could be interpreted to mean that the fluid in the patient's lungs has not changed significantly and hence the patient is not experiencing any pulmonary edema. As indicated generally at 704, after day 6 and through day 10, the diagnostic values begin to trend lower. This can be interpreted as increased fluid in the lungs, which correlates to a possible condition of pulmonary edema. The onset of pulmonary edema, in turn, may indicate that the patient's cardiac health is worsening, as the heart is unable to clear the fluid from the lungs.

Accordingly, the histogram analysis sub-system has effectively removed variability caused by the patient's breathing so that meaningful diagnostic values are derived to provide insight into the patient's pulmonary edema condition. Stated more generally, the histogram analysis sub-system effectively removes variability caused by a first factor so that diagnostic values which more accurately reflect a second factor can be determined.

In response to the trend analysis, the implantable device may additionally be directed to apply pacing therapy. For instance, if the trend of the minimum thoracic impedance crosses a predetermined threshold, the implantable device may adjust the pacing therapy to counteract the deteriorating condition.

Operation

The implantable cardiac device 100 is implanted into a patient and over time gathers data that can be used as parameters for diagnosing heart failure. Histogram analysis may be applied to the data to determine diagnostic values which are indicative of whether a patient's heart condition is improving or worsening. The histogram analysis may be performed on the implantable cardiac device 100, or on an external device, such as programmers 302, 308 or computing system 320, or on a combination of the implantable and external devices.

Figure 8:
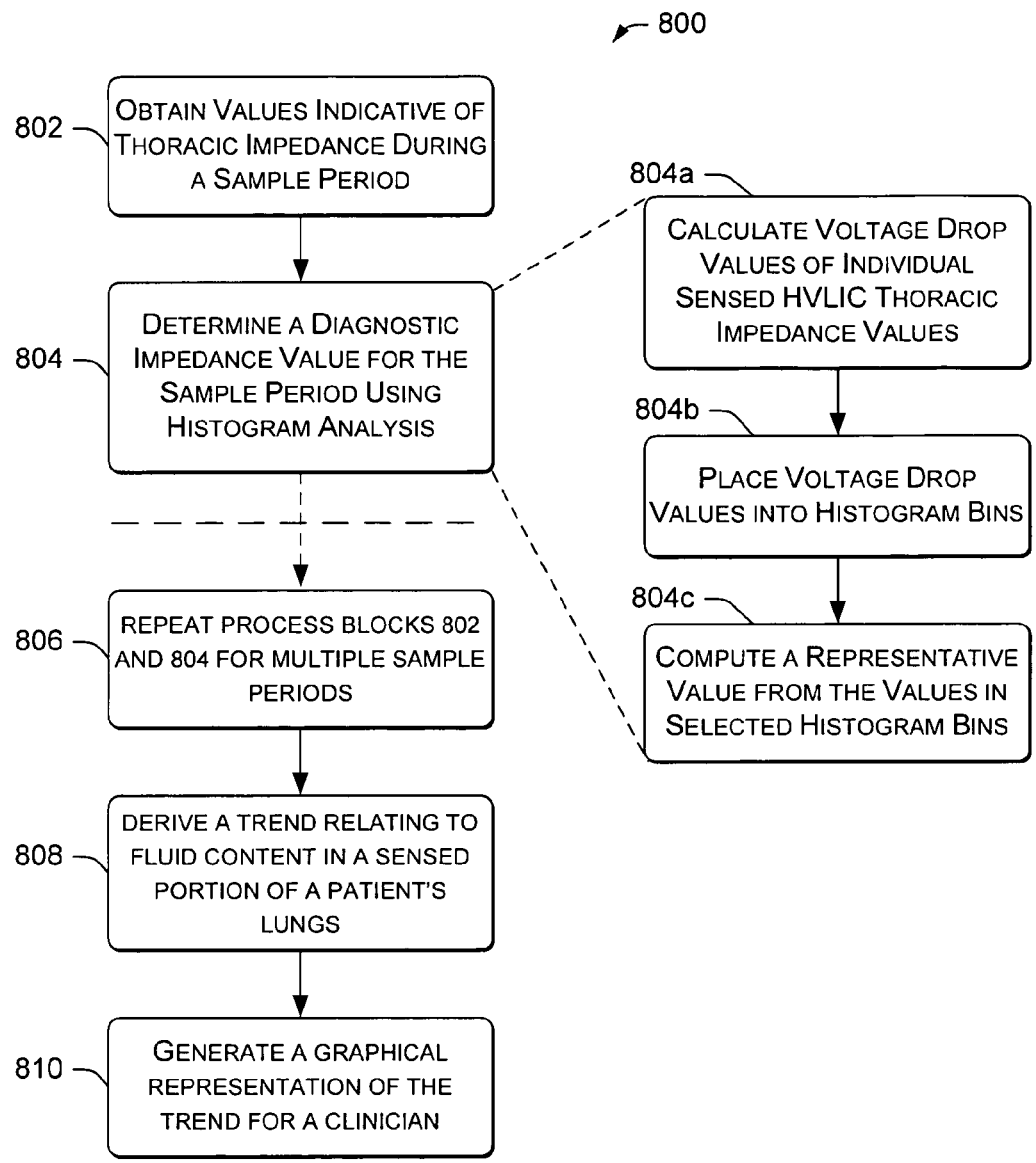
FIG. 8 is a flow diagram of an exemplary process for implementing histogram analysis.

FIG. 8 shows a process 800 for analyzing measured thoracic impedance values using a histogram to identify certain values that might be helpful in diagnosing a patient's cardiac health. In this implementation, the operations of process 800 are summarized in individual blocks. The operations may be performed in hardware and/or as machine-readable instructions (software or firmware) that can be executed by a processor, such as the microcontroller used in the implantable device or the processing units at programmers 302, 308 and computing system 320.

At block 802, the process obtains values indicative of thoracic impedance during a sample period that includes multiple respiratory cycles. The values are sensed by the implantable device over a period of time corresponding to the sample period. As one example, the sensed values comprise the HVLIC values, such as those shown in timeline 406 of FIG. 4, which are indicative of thoracic impedance.

At block 804, the process determines a diagnostic impedance value for the sample period using histogram analysis. The parameters measured within the sample period can be allocated across multiple bins. The statistical distribution may then be analyzed to extract information regarding thoracic impedance.

As one example implementation of this operation, a sub-process for determining a minimum thoracic impedance value is described in relation to blocks 804a-804c. The minimum thoracic impedance value is particularly interesting because it is traditionally very difficult to measure directly. Thoracic impedance is influenced by the patient's respiration and finding a minimum value over numerous respiratory cycles is hard to pinpoint. Although minimum thoracic impedance value is described here, the sub-process is equally applicable for determining other diagnostic impedance values from the histogram analysis.

At block 804*a*, the process calculates voltage drop values of individual sensed HVLIC thoracic impedance values. An example of such a process is described above in relation to FIGS. 4-5.

At block 804*b*, the voltage drop values are allocated to histogram bins, such as those shown in and described in relation to FIG. 6. Any appropriate number of bins can be employed, with suitable numbers ranging from 10 to 20 bins. However, more or less bins outside of this range are equally consistent with the concepts described herein.

At block 804*c*, a representative value of the voltage drop values in one or more selected bins is computed. The representative value can be derived, for instance, by adding the values in each bin and dividing the sum by the total number of values in the bin. The value may further be calculated by averaging over more than one bin. Further, each bin in the histogram may be processed, or less than all bins may be processed, depending upon the application. When finding the minimum thoracic impedance, the lower valued bins are considered. The number of bins used in the analysis is not critical, with an example number being approximately 20% of the total number of bins. Numbers of bins outside of this range are equally consistent with the concepts described herein.

The operations of blocks 802 and 804 provide a diagnostic impedance value (e.g., minimum thoracic impedance) for a given sample period. The histogram analysis can be repeated over different sample periods to derive a trend relating to the cardiac health of the patient. Accordingly, at block 806, the process optionally repeats process blocks 802 and 804 to compute diagnostic values for multiple sample periods.

At block 808, the process 800 derives a trend of the diagnostic impedance values produced over multiple sample periods. The trend can indicate whether fluid content in the patient's lungs is increasing or decreasing, which in turn provides insight as to whether the patient is experiencing pulmonary edema. Such a trend, taken alone or in combination with other parameter trends, can be used to assess the patient's cardiac condition.

At block 810, the trend can be presented as part of a graphical representation to a care provider. For instance, FIG. 7 shows a graphical representation where minimum thoracic impedance values suggest that fluid content in the patient's lungs is stable for a period of time and subsequently begins to rise. Alternatively or additionally to the graphical representation, a diagnostic statement could be provided for the care provider. For instance, a diagnostic statement consistent with FIG. 7 might state that "the patient's minimum thoracic impedance values were relatively stable from days 1-6, but have increased each of the following days. Such values are consistent with increasing fluid in the lungs associated with a worsening pulmonary edema condition." This is but one of many examples which are consistent with the concepts described above and below.

CONCLUSION

The foregoing discussion describes techniques for diagnosing heart failure using histogram analysis. Although the inventive principles have been described in language specific to structural features and/or methodological acts, it is to be understood that the subject matter defined in the appended claims is not necessarily limited to the specific features or acts described. Rather, the specific features and acts are disclosed as exemplary forms of implementing the claimed subject matter.

What is claimed is:

1. A system indicating a pulmonary edema condition comprising:
    an implantable cardiac device to sense values indicative of thoracic impedance from a patient over multiple respiratory cycles; and
    a histogram analysis sub-system to categorize a set of thoracic impedance values using a histogram and to determine a diagnostic value from the set of thoracic impedance values based on the histogram;
    wherein the thoracic impedance values are distributed across multiple bins of the histogram, each bin representing a unique impedance value range in the histogram;
    wherein only lowest-valued bins of the histogram are selected to determine the diagnostic value; and
    wherein the diagnostic value indicates whether a pulmonary edema condition of a patient is improving or worsening.

2. A system as recited in claim 1, wherein the histogram analysis sub-system is configured as part of the implantable cardiac device.

3. A system as recited in claim 1, wherein the histogram analysis sub-system is configured in an external device separate from the implantable cardiac device.

4. A diagnostic system comprising:
    a memory to store multiple sets of thoracic impedance values measured from a patient over multiple respiratory cycles; and
    a processing unit configured to, for each individual set, distribute the thoracic impedance values in that set in a histogram based upon the impedance value and determine a minimum thoracic impedance value for each individual set by analyzing the distribution of the thoracic impedance values in the corresponding histogram;
    wherein the processing unit is further configured to derive a trend of only the minimum thoracic impedance values; and
    wherein the processing unit is further configured to interpret the trend of only the minimum impedance values as one of an improving pulmonary edema condition or a worsening pulmonary edema condition.

5. A diagnostic system as recited in claim 4, wherein the processing unit is further configured to interpret the trend as one of an improving cardiac condition or a worsening cardiac condition.

6. A diagnostic system as recited in claim 4, further comprising a user interface to present the trend in a user-perceptible form.

7. A system indicating a pulmonary edema condition comprising:
    means for storing thoracic impedance values measured from a patient over multiple respiratory cycles;
    means for distributing the thoracic impedance values across multiple bins of a histogram, each bin representing a unique impedance value range in the histogram; and
    means for determining only a minimum thoracic impedance from the thoracic impedance values in one or more selected bins of the histogram by selecting only lowest-valued bins of the histogram;
    means for deriving a trend of the minimum thoracic impedances determined over time; and means for presenting the trend and a possible interpretation of the trend as one of an improving pulmonary edema condition or a worsening pulmonary edema condition.

8. A system as recited in claim 7, further comprising means for applying pacing therapy in an event that the minimum thoracic impedance crosses a predetermined threshold.

9. A method indicating a pulmonary edema condition comprising:
 sense values indicative of thoracic impedance from a patient over a sample period by calculating voltage drop values of individual HVLIC values;
 storing data indicative of the thoracic impedance measured from a patient during the sample period that includes multiple respiratory cycles;
 forming a histogram of the data by placing the voltage drop values into histogram bins, each bin representing a unique impedance value range in the histogram; and
 deriving a diagnostic value based on selecting only lowest valued bins of the histogram;
 wherein the diagnostic value is used to determine whether a pulmonary edema condition of a patient is improving or worsening.

* * * * *